United States Patent [19]

Wheeler et al.

[11] Patent Number: 4,526,723
[45] Date of Patent: Jul. 2, 1985

[54] BIOCIDAL ENOL ESTERS OF NON-ORTHO SUBSTITUTED 2-ARYL-1-3-CYCLOALKANEDIONE COMPOUNDS

[75] Inventors: Thomas N. Wheeler; Mathias H. J. Weiden, both of Charleston, W. Va.

[73] Assignee: Union Carbide Corporation, Danbury, Conn.

[21] Appl. No.: 510,731

[22] Filed: Jul. 5, 1983

Related U.S. Application Data

[63] Continuation of Ser. No. 946,311, Sep. 27, 1978, abandoned.

[51] Int. Cl.$^3$ .................. C11C 3/04; C07C 69/03
[52] U.S. Cl. .................. 260/410.5; 71/103; 71/106; 71/122; 260/399; 260/400; 260/401; 260/402; 260/402.5; 260/404; 260/410; 260/465 D; 260/463; 560/100; 560/106; 560/118; 560/128; 560/255
[58] Field of Search .............. 424/331; 560/255, 100, 560/106, 118, 128; 260/399, 400, 401, 402, 402.5, 404, 410, 410.5, 465 D; 71/106, 103, 122

[56] References Cited

U.S. PATENT DOCUMENTS

| | | | |
|---|---|---|---|
| 3,273,992 | 9/1966 | Treves et al. | 71/2.3 |
| 3,321,291 | 5/1967 | Weil | 71/2.3 |
| 3,378,580 | 4/1968 | Roberts et al. | 260/488 |
| 4,104,043 | 8/1978 | Durden, Jr. | 71/107 |
| 4,209,532 | 6/1980 | Wheeler | 424/331 |
| 4,283,348 | 8/1981 | Wheeler | 424/331 X |
| 4,338,122 | 7/1982 | Wheeler | 424/331 X |
| 4,386,086 | 5/1983 | Manning et al. | 424/331 X |
| 4,436,666 | 3/1984 | Wheeler | 424/331 X |

OTHER PUBLICATIONS

Gren, CA 56–p. 1291.
Grens,–CA vol. 83 (1975)–p. 477–113469s.
Grens et al., "Nature of Assoc. Etc." (1972) CA 78.110,026f (1973).

Primary Examiner—Thomas A. Waltz
Attorney, Agent, or Firm—Gerald L. Coon

[57] ABSTRACT

Non-ortho substituted 2-aryl-1,3-cycloalkanedione enol ester compounds exhibit outstanding acaricidal and herbicidal activity.

12 Claims, No Drawings

BIOCIDAL ENOL ESTERS OF NON-ORTHO SUBSTITUTED 2-ARYL-1-3-CYCLOALKANEDIONE COMPOUNDS

This application is a continuation of application Ser. No. 946,311, Sept. 27, 1978, now abandoned.

This invention relates to biocidal non-ortho substituted 2-aryl-1,3 cycloalkanedione enol ester compounds and methods of preparing them. This invention is also directed to herbicidal and acaricidal compositions as well as methods of controlling these plant pests which utilize the compounds of the instant invention as the pesticidally effective component.

More particularly, this invention relates to compounds of the formula:

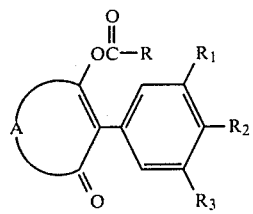

wherein:

R is a halogen, alkyl, alkenyl, alkynyl, bicycloalkyl, bicycloalkenyl, cycloalkyl, cycloalkenyl, haloalkyl, phenyl, phenylalkyl, naphthyl or naphthylalkyl group, all of which, other than the halogen group, may be substituted with one or more alkyl, cyano, nitro, alkoxy, aryloxy, halogen, haloalkyl, alkoxyalkyl, alkylthio, arylthio, alkylsulfinyl, arylsulfinyl, alkylsulfonyl, arylsulfonyl, alkylsulfinylalkyl, alkylsulfonylalkyl, alkylthioalkyl or dialkylamino substitutuent, provided that R may not include more than thirty aliphatic carbon atoms;

$R_1$, $R_2$, and $R_3$ may not individually include more than ten aliphatic carbon atoms and are individually hydrogen, haloalkyl, polyhaloalkyl, alkoxy, halogen or alkyl groups;

A is an alkylene or alkenylene chain containing two or three carbon atoms which chain may be substituted by one or more substituents which may be the same or different selected from:

(a) substituents which may not include more than ten aliphatic carbon atoms selected from: an alkyl, alkenyl, cycloalkyl or cycloalkenyl group, which groups may be further substituted by one or more cyano, halogen, nitro; alkoxy, aryloxy, alkylthio, arylthio, alkylsulfinyl, arylsulfinyl, alkylsulfonyl, arylsulfonyl, acylamido, or dialkylamino substituents in any combination; and a phenyl group which may be substituted by one or more alkyl, alkenyl, cycloalkyl, cycloalkenyl, cyano, halogen, nitro, alkoxy, aryloxy, alkylthio, arylthio, alkylsulfinyl, arylsulfinyl, alkylsulfonyl, arylsulfonyl, acylamido or dialkylamino substituents in any combination;

(b) a divalent alkylene or alkenylene group having from 2 to 20 carbon atoms completing a 3,4,5,6 or 7 membered carbon ring with the proviso that when A is a hydrocarbon chain containing two carbon atoms, a six membered fused polycyclic ring structure completed by a divalent butylene group may not have conjugated double bonds in said six membered ring.

It has been discovered that compounds of the following formula:

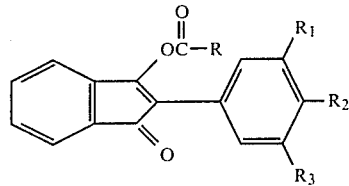

wherein R, $R_1$, $R_2$ and $R_3$ are as defined above, do not exhibit acaricidal or herbicidal activity. Thus, this class of compounds have been excluded from the generic formula defining the compounds of the instant invention.

As used within this specification, the prefix "aryl" designates any organic radical derived from an aromatic hydrocarbon by the removal of one hydrogen atom. Preferably, aryl designates a phenyl or naphthyl moiety.

PREFERRED EMBODIMENT OF THE INVENTION

All compounds within the purview of the above generic formula exhibit acaricidal and herbicidal activity to a greater or lesser extent. Some of these compounds exhibit very powerful acaricidal or herbicidal activity in extremely small dosages while others require larger dosages to be pesticidally effective. In general, the compounds of this invention that exhibit the highest order of herbicidal activity also exhibit the highest order of acaricidal activity. The compounds of the instant invention are particularly effective against mites, both in the egg stage and the adult stage.

It has also been found that some of the pesticidal compositions of this invention exhibit excellent fumigant properties. Fumigant activity is defined as the ability of a pesticide to exert its pesticidal activity on an untreated surface or plant from a treated surface or plant in close proximity to the untreated area. It is believed that this property is caused, at least in part, by the low vapor pressure of the compounds allowing them to volatilize from a treated surface thereby exerting their pesticidal effects on nearby untreated areas. In addition, these compounds are relatively non-toxic to mammals when used in amounts sufficient to kill acarids or undesirable plant growth.

Preferred because of their higher level of acaricidal and herbicidal activity are the 2-phenyl-1,3-cycloalkanedione enol ester compounds of this invention in which the substituents are defined as follows:

For the 2-phenyl-1,3-cyclopentanedione enol esters compounds of the following formula:

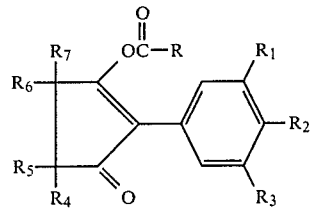

R is an alkyl group having from 1 to 30 carbon atoms, preferably from 6 to 30 carbon atoms, most preferably from 6 to 18 carbon atoms;

$R_1$, $R_2$, $R_3$ are individually hydrogen, alkyl, halogen or trihalomethyl groups;

$R_5$ and $R_7$ are hydrogen; and $R_4$ and $R_6$ are individually hydrogen or alkyl groups, particularly $C_1$–$C_4$ alkyl groups; or $R_4$ and $R_6$ taken together form an alkylene chain having four carbon atoms completing a six membered fused polycyclic ring structure.

For the 2-phenyl-1,3-cyclopentanedione enol ester compounds of the following formula:

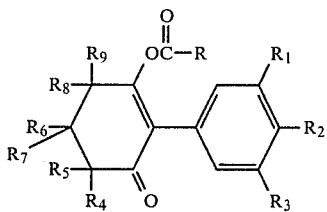

R, $R_1$, $R_2$, and $R_3$ are as defined for the preferred cyclopentanedione compounds above;

$R_4$, $R_5$, $R_6$, $R_7$, $R_8$, $R_9$ are individually hydrogen or alkyl groups, particularly $C_1$–$C_6$ alkyl groups, most particularly methyl groups.

It has been discovered that when R is a branched chain alkyl rather than a straight chain alkyl, the phytotoxicity of the compound decreases. Thus where this quality is preferred, the branched chain alkyl is the preferred R substituent.

The most preferred substituent pattern for the 2-phenyl-1,3-cyclopentanedione enol ester compounds of the instant invention according to the following formula:

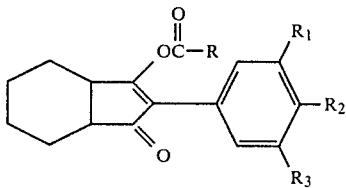

wherein:

R is an alkyl group having from 1 to 30 carbon atoms, preferably from 6–30 carbon atoms, most preferably from 6–18 carbon atoms; and $R_1$, $R_2$ and $R_3$ are individually hydrogen, methyl, chlorine, fluorine or bromine.

For the 2-phenyl-1,3-cyclohexanedione enol ester compounds of this invention, the most preferred substituent pattern is that in which:

R, $R_1$, $R_2$, and $R_3$ are as defined for the most preferred cyclopentanedione compounds above;

$R_4$, $R_5$, $R_6$, $R_7$, $R_8$, and $R_9$ are individually hydrogen or $C_1$–$C_4$ alkyl groups, preferably methyl. This type of substituent pattern is preferred especially when $R_4$ and $R_8$ are hydrogen and $R_5$ and $R_9$ are alkyl substituted. Especially preferred are compounds wherein $R_4$, $R_5$, $R_8$ and $R_9$ are hydrogen and either or both of $R_6$ and $R_7$ are alkyl substituted.

The individually preferred compounds of the instant invention are:

3-decanoyloxy-2-(4'methylphenyl)-5,5-dimethyl-2-cyclohexenone;

3-octanoyloxy-2-(4'methylphenyl)-5,5-dimethyl-2-cyclohexenone;

3-palmitoyloxy-2-(4'-methylphenyl)-5,5-dimethyl-2-cyclohexenone; and 3-(2,2-dimethyloctanoyloxy)-2-(4'-methylphenyl)-5,5-dimethyl-2-cyclohexenone.

The enol ester compounds of this invention can be conveniently prepared by a variety of methods. The preferred method which utilizes the 2-aryl-1,3-cycloalkanedione parent compound as the precursor is illustrated by the general reaction scheme set forth below in which R, $R_1$–$R_3$ inclusive, and A are as defined above and X is halogen, hydroxyl, or

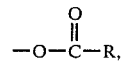

except as noted.

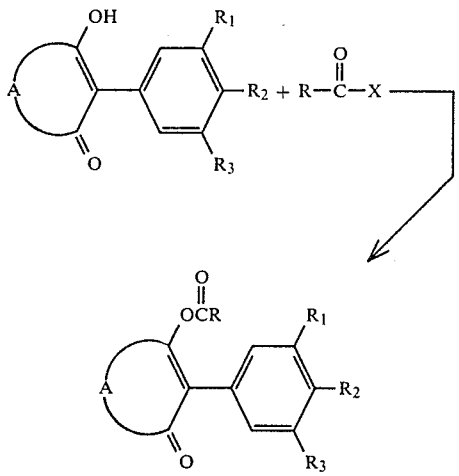

In this reaction scheme one equivalent of the corresponding 2-phenyl-1,3-cyclopentanedione compound is reacted with an appropriately substituted acid, acid halide, or acid anhydride compound in the presence of at least one equivalent of an acid acceptor, preferably in an inert solvent.

The acid acceptor utilized in this reaction scheme can be either an organic or inorganic base. Illustrative of organic bases that are useful as acid acceptors are tertiary amines, such as triethylamine, pyridine, trimethylamine or 1,4-diazobicyclo[2.2.2]octane; or alkali metal alkoxides, as, for example, sodium ethoxide; potassium hydroxide and sodium hydroxide are illustrative of inorganic bases that are useful as acid acceptors. Preferred acid acceptors are triethylamine, pyridine or trimethylamine.

In general, any organic solvent that is inert to the reactants or reaction conditions may be employed in the reaction scheme shown above. Illustrative of organic solvents which are generally suitable for use in the conduct of these reactions are saturated, unsaturated and aromatic hydrocarbons, e.g. hexane, cyclohexane, octane, cyclohexane, dodecane, naphtha, decalin. kerosene, cycloheptane, benzene, toluene, xylene, napthalene or the like; ethers such as dioxane, tetrahydrofuran, diethyl ether, tetrahydropyran, 1,2-dimethoxybenzene, 1,2-diethylbenzene, the dialkyl ethers of ethylene glycol, of propylene glycol or chlorinated aliphatic hydrocarbons as, for example, chloroform, dichloromethane, 1,1-dichloroethane, carbon tetrachloride, or the like.

The reactions illustrated by the general scheme given above may also be conducted in a solvent which functions as an acid acceptor. Illustrative of such multifunctional solvents are N,N-dimethylaniline, pyridine, α-picoline, lutidine, collodine or any like aromatic or heterocyclic tertiary amine compound.

The reactions illustrated by the general scheme given above are neither temperature nor pressure sensitive and can be conducted over a broad temperature and pressure range to yield the desired product. Preferably, these reactions are conducted at a temperature of from −40° C. to about 120° C. and at atmospheric or autogeneous pressure.

The acid halide, acid, and acid anhydride compounds utilized as reactants in the above reaction scheme are known classes of compounds that can either be obtained from commercial sources or prepared in accordance with conventional methods known to those skilled in the art.

The 2-phenyl-1,3-cycloalkanediones utilized as reactants in the above synthesis scheme can be conveniently prepared in accordance with a number of synthetic procedures.

For example, the 2-aryl-1,3-cyclopentanediones may be prepared by the base-promoted cyclization of the appropriate α-aryl levulinic acid ester. This is illustrated by reacting ethyl-5-(2',4'-dichlorophenyl)-4-ketopentanoate with sodium ethoxide in the presence of a toluene solvent to form 2-(2',4'-dichlorophenyl)-1,3-cyclopentanedione. The σ-aryl levulinic acid esters used as reactants in the above synthesis can be prepared using conventional esterification techniques of the appropriate σ-aryl levulinic acids. The σ-aryl levulinic acids can be prepared by the condensation of benzyl cyanides with succinate esters followed by hydrolysis and decarboxylation of the intermediate σ-cyano-σ-aryl levulinic esters.

The 8-arylbicyclo[4.3.0]nonane-7,9-diones are prepared by the base promoted isomerization of the appropriate γ-benzylidene lactone. This is illustrated by reacting 4,5,6,7,8,9-hexahydro-3-(2'-methylbenzylidene)phthalide with soduim ethoxide in the presence of a toluene solvent to form 8-(2'-methylphenyl)-bicyclo[4.3.0]nonane-7,9-dione. The γ-benzylidene lactone can be formed by the acid catalyzed lactonization of the corresponding σ-aryl levulinic acid, a synthesis method known to those skilled in the art.

Preferably, those 2-aryl-1,3-cyclopentanedione compounds, wherein (1) there is a fused ring on the cyclopentane moiety and (2) the 2-phenyl substituent is itself substituted with halogens, may be formed by pinacol rearrangement as outlined in the Journal of The American Chemical Society, (99:3) Feb. 2, 1977, pages 961–962. These synthetic procedures are described in more detail in U.S. Pat. No. 4,283,348 issued Aug. 11, 1981 and U.S. Pat. No. 4,338,122 issued July 6, 1982.

The 2-phenyl-1,3-cyclohexanediones can be prepared by heating the corresponding 6-aryl-5-ketopolyalkyl hexanoic acid compound with sulfuric acid or alternatively by treating the corresponding 6-aryl-5-ketopolyalkylhexanoic acid ester with base. Both the hexanoic acid or acid esters used to synthesize the 2-phenyl-1,3-cyclohexanedione compounds are either obtainable from commercial sourses or prepared by conventional methods known to those skilled in the art.

The preparation of the 2-phenyl-1,3-cyclohexanediones are described in more detail in my copending U.S. patent application, Ser. No. 781,985 entitled, "BIOCIDAL 2-ARYL-1,3-CYCLOHEXANEDIONE COMPOUNDS AND ALKALI METALS AND AMMONIUM SALTS THEREOF", filed Mar. 28, 1977, now U.S. Pat. No. 4,209,532.

The following specific examples are presentd to more particularly illustrate the process of this invention and their use in preparing the compounds of this invention.

EXAMPLE I

Preparation of 2-(4'-methylphenyl)-5,5-dimethyl-1,3-cyclohexanedione

This dione was prepared by acid cyclization of ethyl 6-(4'methylphenyl)-6-cyano-5-keto-3,3-dimethylhexanoate. Preparation of the hexanoate is described in Part A and of the dione in Part B.

Part A: Preparation of ethyl 6-(4'-methylphenyl)-6-cyano-5-keto-3,3-dimethylhexanoate A 2 liter flask was equipped with a mechanical stirrer, a Dean-stark trap, a reflux condenser, an addition funnel, and a nitrogen inlet. The glassware was dried thoroughly, and the flask charged with 280 ml of dry ethanol. To the stirred reaction mixture was added 22.73 g (0.99 mol) of sodium spheres in portions. After the spontaneous reaction had subsided, the mixture was heated until the sodium had dissolved. While the reaction mixture was refluxed, a mixture of 220.0 g (1.02 mol) of ethyl 3,3-dimethylglutarate and 100.0 g (0.76 mol) of 4-methylbenzyl cyanide was added dropwise. The reaction mixture was refluzed for about 2 hours after the addition was complete and then about 75% of the ethanol was removed via the Dean-stark trap. The reaction mixture was cooled and poured into ice water. The basic aqueous solution was extracted twice with 275 ml portions of ether, acidified with cold 6N HCl, and extracted twice again with 250 ml portions of ether. The ether extracts of the acid solution were washed 4 times with 300 ml of water, dried with $MgSO_4$, and the ether removed to leave 156.77 g (68% yield) of a yellow oil which was shown by IR and NMR to be the desired product.

Part B: Preparation of 2-(4'-methylphenyl)-5,5-dimethyl-1,3-cyclohexanedione A 3 liter flask was equipped with a mechanical stirrer, reflux condenser, addition funnel, $N_2$ inlet, and thermometer. The flask was charged with 156.77 g (0.52 mol) of ethyl 6-(4'-methylphenyl)-6-cyano-5-keto-3,3-dimethylhexanoate dissolved in 370 ml of glacial acetic acid, followed by 132 ml of water, and finally 132 ml of concentrated sulfuric acid was added. The reaction mixture was refluxed for 48 hours, cooled to room temperature and 600 ml of water and 300 ml of isopropyl ether added. This two-phase system was refluxed for 1 hour, cooled in an ice bath, and filtered. The precipitate was washed thoroughly with water and isopropyl ether, then dried overnight in a vacuum oven to give 68.09 g (57% yield) of the desired product as a pale yellow powder; m.p. 199.5°–201.5° C.

The compound prepared by the above synthesis has the following structure:

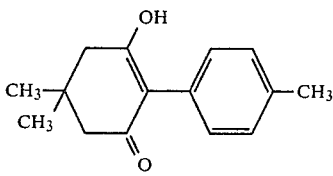

EXAMPLE II

Preparation of 2-(3′-chlorophenyl)-5,5-dimethyl-1,3-cyclohexanedione

This dione was prepared by the acid cyclization of ethyl 6-(3′chlorophenyl)-6-cyano-5-keto-3,3-dimethylhexanoate. Preparation of the hexanoate is described in Part A and of the dione in Part B below.

Part A: Preparation of ethyl 6-(3′chlorophenyl)-6-cyano-5-keto-3,3-dimethylhexanoate Starting with 75.0 g (0.495 mol) of 3-chlorobenzyl cyanide, 160.58 g (0.743 mol) of diethyl 3,3-dimethylglutarate, 14.80 g (0.643 mol) of sodium, and 260 ml of dry ethanol a total of 108.08 g (71% yield) of the desired product was obtained using the procedure described in Example I, Part A.

Part B: Preparation of 2-(3′-chlorophenyl)-5,5-dimethyl-1,3-cyclohexanedione Starting with 108.08 g (0.351 mol) of ethyl 6-(3′-chlorophenyl)-6-cyano-5-keto-3,3-dimethylhexanoate, 316 ml of acetic acid, 105 ml of water, and 105 ml of concentrated sulfuric acid, and utilizing the procedure described in Example 1, Part B, 40.82 g (46% yield) of 2-(3′-chlorophenyl)-5,5-dimethyl-1,3-cyclohexanedione was obtained as a white solid, m.p. 155°–58° C.

The compound synthesized in the above preparation has the following structure:

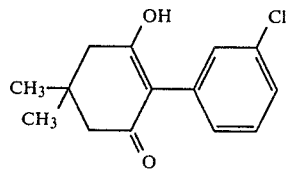

EXAMPLE III

Preparation of 3-decanoyloxy-2-(4′-methyl)-5,5-dimethyl-2-cyclohexenone

A 100 ml flask was equipped with a magnetic stirrer and an addition funnel with $N_2$ inlet. The glassware was dried thoroughly and charged with 3.00 g (0.0130 mol) of 2-(4′-methylphenyl)-5,5-dimethyl-1,3-cyclohexanedione, 30 ml of methylene chloride, and 2.63 g (0.0260 mol) of triethylamine. The reaction mixture was cooled in an ice bath, and 1.87 g (0.0098 mol) of decanoyl chloride was added dropwise. The reaction mixture was allowed to stir overnight at room temperature, then the methylene chloride removed on the rotary evaporator. The residue was triturated with ether and filtered. The ether was washed once with water, twice with cold 1N HCl, and twice with water. The ether was dried with $MgSO_4$ and removed to leave 2.8 g viscous, colorless oil as the desired product.

Calcd. for $C_{25}H_{36}O_3$: C, 78.08; H, 9.44; Found: C, 78.08; H, 9.43.

The compound synthesized in the above preparation has the following structure:

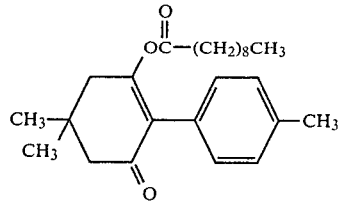

EXAMPLE IV

Preparation of 3-octanoyloxy-2-(4′-methylphenyl)-5,5-dimethyl-2-cyclohexenone

Using the procedure described in Example III and starting with 3.00 g (0.0130 mol) of 2-(4′-methylphenyl)-5,5-dimethyl-1,3-cyclohexanedione, 1.59 g (0.0098 mol) of octanoyl chloride, 2.63 g (0.0260 mol) of triethylamine, and 30 mol of methylene chloride, 2.5 g (71% yield) of a clear, colorless oil was obtained as the desired product.

Calcd. for $C_{23}H_{32}O_3$: C, 77.49; H, 9.05; Found: C, 77.56; H, 9.11.

The compound synthesized in the above preparation has the following structure:

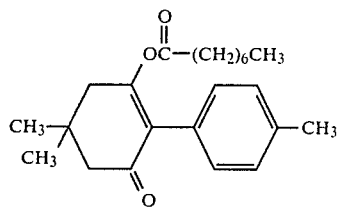

EXAMPLE V

Preparation of 3-(2,2-dimethyloctanoyloxy)-2-(4′-methylphenyl)-5,5-dimethyl-2-cyclohexenone Using the procedure described in Example III and starting with 3.00 g (0.0130 mol) of 2-(4′-methylphenyl)-5,5-dimethyl-1,3-cyclohexanedione, 1.87 g (0.0098 mol) neodecanoyl chloride, 2.63 g (0.0260 mol) of triethylamine, and 30 ml of methylene chloride, 2.80 g (74% yield) of the desired product was obtained as a clear, colorless oil.

Calcd. for $C_{25}H_{36}O_3$: C, 78.08; H, 9.44; Found: C, 78.42; H, 9.63.

The compound synthesized in the above preparation has the following structure:

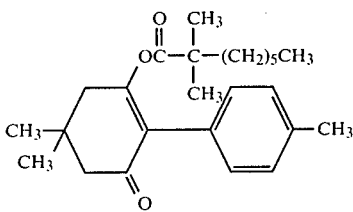

EXAMPLE VI

Preparation of
3-palmitoyloxy-2-(4'-methylphenyl)-5,5-dimethyl-2-cyclohexenone

Using the procedure described in Example III and starting with 3.00 g (0.0130 mol) of 2-4'-methylphenyl)-5,5-dimethyl-1,3-cyclohexanedione, 2.69 g (0.0098 mol) of palmitoyl chloride, 2.63 g (0.0260 mol) of triethylamine, and 30 ml of methylene chloride, 3.1 g (67% yield) of a clear, colorless oil was obtained as the desired product.

Calcd. for $C_{31}H_{48}O_3$: C, 79.44; H, 10.32; Found: C, 79.44; H, 10.35.

The compound synthesized in the above preparation has the following structure:

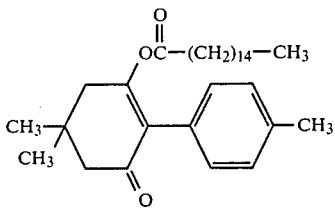

Additional compounds were prepared in a manner similar to those illustrated in the above examples and are listed in Table I with a melting point or an elemental analysis.

The following compounds are illustrative of the compounds of the instant invention:

(1) 3-nonanoyloxy-2-(4'-fluorophenyl)-5,5-dimethyl-2-cyclohexenone
(2) 3-octanoyloxy-2-(4'-trifluoromethyl)-5,5-dimethyl-2-cyclohexenone
(3) 3-(2,2-dimethyloctanoyloxy)-2-(4'-chlorophenyl)-5,5-dimethyl-2-cyclohexenone
(4) 3-heptanoyloxy-2-(3',4'-dichlorophenyl)-5,5-dimethyl-2-cyclohexenone
(5) 3-(2-ethylhexanoyloxy)-2-(4'-methoxyphenyl)-5-methyl-2-cyclohexenone
(6) 3-hexanoyloxy-2-(3'-methoxy-4'-chlorophenyl)-5,5-dimethyl-2-cyclohexenone
(7) 3-palmitoyloxy-2-(3'-trifluoromethyl-4'-chlorophenyl)-5,5-dimethylcyclohexenone
(8) 3-decanoyloxy-2-(3'-methyl-4'-methoxyphenyl)-5,5-dimethyl-2-cyclohexenone
(9) 7-benzoyloxy-8-(3',4'-dimethylphenyl)-2-methylbicyclo[4.3.0]non-7-en-9-one
(10) 7-octanoyloxy-8-(4'-chlorophenyl)bicyclo[4.3.0]non-7-en-9-one
(11) 3-heptanoyloxy-2-(4'-methylphenyl)-4,5,6,7-tetrahydro-2-indenone
(12) 3-(2,2-dimethyloctanoyloxy)-2-(4'-trifluoromethylphenyl)-4,5,6,7-tetrahydro-2-indenone
(13) 3-hexanoyloxy-2-(4'-chlorophenyl)-4,5,6,7-tetrahydro-2-indenone
(14) 5-octanoyloxy-4-(4'-methoxyphenyl)tricyclo[5.2.1.0$^{2,6}$]dec-4-en-3-one
(15) 5-decanoyloxy-4-(3'-chlorophenyl)tricyclo[5.2.1.0$^{2,6}$]dec-4-en-3-one
(16) 4-stearoyloxy-3-(3',4'-dimethylphenyl)bicyclo[3.3.0]oct-3-en-2-one
(17) 4-benzoyloxy-3-(3'-methoxy-4'-chlorophenyl)bicyclo[3.2.0]hept-3-en-3-one
(18) 3-pentanoyloxy-4,5-dimethyl-2-(4'-methylphenyl)-2-cyclopentenone
(19) 3-heptanoyloxy-5-methyl-2-phenyl-2-cyclopentenone
(20) 3-octanoyloxy-2-(4'-chlorophenyl)spiro[4.5]dec-2-en-1-one
(21) 3-(2-ethylhexanoyloxy)-2-(4'-methylphenyl)spiro[4.4]non-2-en-1-one
(22) 4-decanoyloxy-3-(3',4'-dimethylphenyl)bicyclo]3.3.0]octa-3,6-dienone
(23) 4-octanoyloxy-3-(4'-chlorophenyl)bicyclo[3.2.0]hept-3-en-2-one
(24) 3-octanoyloxy-2-(3'-trifluoromethyl-5'-methoxyphenyl)-5,5-dimethyl-2-cyclohexenone
(25) 3-octanoyloxy-2-(3',5'-dichlorophenyl)-5,5-dimethyl-2-cyclohexenone
(26) 3-pivaloyloxy-2-(3'-methyl-4'-methoxy-5'-chlorophenyl)-5,5-dimethyl-2-cyclohexenone
(27) 3-heptanoyloxy-2-(3',4',5'-trichlorophenyl)-5,5-dimethyl-2-cyclohexenone
(28) 3-(2,2-dimethyloctanoyloxy)-2-(3'-methoxy-4'-trifluoromethylphenyl)-5,5-dimethyl-2-cyclohexenone
(29) 3-butanoyloxy-2-(4'-ethylphenyl)-5,5-dimethyl-2-cyclohexenone
(30) 3-octanoyloxy-2-(4'-methylphenyl)-2-cyclohexenone
(31) 3-pentanoyloxy-2-(4'-methylphenyl)-5-methyl-2-cyclohexenone
(32) 3-acetoxy-2-(4'-chlorophenyl)-4,6-dimethyl-2-cyclohexenone
(33) 3-(7-phenylheptanoyloxy)-2-(4'-trifluoromethylphenyl)-2-cyclopentenone
(34) 3-(6-chlorohexanoyloxy)-2-(4'-methylphenyl)-2-cyclopentenone
(35) 3-(4'-chlorobenzoyloxy)-2-(4'-chlorophenyl)-2-cyclopentenone
(36) 3-(4'-dimethylaminophenylcarbonyloxy)-2-(3',4'-dichlorophenyl)-2-cyclopentenone
(37) 3-(4'-methylthiophenylcarbonyloxy)-2-(4'-methoxyphenyl)-2-cyclopentenone
(38) 3-trifluoroacetoxy-4-ethyl-2-(3',4'-dichlorophenyl)-2-cyclopentenone
(39) 3-(2-ethylhexanoyloxy)-4,5-diethyl-2-phenyl-2-cyclopentenone
(40) 3-naphthylcarbonyloxy-2-(4'-trifluoromethylphenyl)-2-cyclopentenone
(41) 3-palmitoyloxy-2-(3'-methylphenyl)-5-methyl-2-cyclopentenone
(42) 3-octanoyloxy-2-(4'-chlorophenyl)-5-cyanomethyl-2-cyclopentenone
(43) 3-butanoyloxy-2-(3',4'-dimethylphenyl)-5-nitromethyl-2-cyclopentenone
(44) 3-methylthioacetoxyl-2-(4'-methylphenyl)-5-ethyl-2-cyclopentenone
(45) 3-cyclopropylcarbonyloxy-2-(4'-chlorophenyl)-5-(n-propylsulfinylmethyl)-2-cyclopentenone
(46) 3-(4'-methoxyphenylcarbonyloxy)-5-phenylsulfonylmethyl-2-cyclopentenone

(47) 7-acetoxy-8-(4'-methylphenyl)bicyclo[4.3.0]non-7-en-9-one

(48) 7-(2-ethylhexanoyloxy)-8-(4'-chlorophenyl)bicyclo[4.3.0]non-7-en-9-one

(49) 3-ethanoyloxy-2-(4'-methylphenyl)-5,5-dimethyl-2-cyclohexenone

(50) 3-isobutanoyloxy-2-(4'-methylphenyl)-5,5-dimethyl-2-cyclohexenone

(51) 3-(2-ethylbutanoyloxy)-2-(4'-methylphenyl)-5,5-dimethyl-2-cyclohexenone

(52) 3-hexanoyloxy-2-(4'-methylphenyl)-5,5-dimethyl-2-cyclohexenone

(53) 3-(2-ethylhexanoyloxy)-2-(4'-methylphenyl)-5,5-dimethyl-2-cyclohexenone

(54) 3-(2,2-dimethyloctanoyloxy)-2-(4'-methylphenyl)-5,5-dimethyl-2-cyclohexenone

(55) 3-octanoyloxy-2-(4'-methylphenyl)-5,5-dimethyl-2-cyclohexenone

(56) 3-decanoyloxy-2-(4'-methylphenyl)-5,5-dimethyl-2-cyclohexenone

(57) 3-palmitoyloxy-2-(4'-methylphenyl)-5,5-dimethyl-2-cyclohexenone

(58) 3-ethanoyloxy-2-(4'-chlorophenyl)-5,5-dimethyl-2-cyclohexenone

(59) 3-(2-ethylhexanoyloxy)-2-(4'-chlorophenyl)-5,5-dimethyl-2-cyclohexenone

(60) 3-ethanoyloxy-2-(3'-chlorophenyl)-5,5-dimethyl-2-cyclohexenone

(61) 3-(2-ethylhexanoyloxy)-2-(3'-chlorophenyl)-5,5-dimethyl-2-cyclohexenone

(62) 3-ethanoyloxy-2-(3'4'-dichlorophenyl)-5,5-dimethyl-2-cyclohexenone

(63) 3-(2-ethylhexanoyloxy)-2-(3',4'-dichlorophenyl)-5,5-dimethyl-2-cyclohexenone

(64) 3-ethanoyloxy-2-(3',4'-dimethylphenyl)-5,5-dimethyl-2-cyclohexenone

(65) 3-pivaloyloxy-2-(3',4'-dimethylphenyl)-5,5-dimethyl-2-cyclohexenone

(66) 3-isobutanoyloxy-2-(3,4'-dimethylphenyl)-5,5-dimethyl-2-cyclohexenone

(67) 3-hexanoyloxy-2-(3'-4'-dimethylphenyl)-5,5-dimethyl)-2-cyclohexenone

(68) 3-(2-ethylhexanoyloxy)-2-(3',4'-dimethylphenyl)-5,5-dimethyl-2-cyclohexenone

(69) 3-palmitoyloxy-2-(3',4'-dimethylphenyl)-5,5-dimethyl-2-cyclohexenone

(70) 3-ethanoyloxy-2-phenyl-5,5-dimethyl-2-cyclohexenone

(71) 3-isobutanoyloxy-2-phenyl-5,5-dimethyl-2-cyclohexenone

(72) 3-pivaloyloxy-2-phenyl-5,5-dimethyl-2-cyclohexenone

(73) 3-hexanoyloxy-2-phenyl-5,5-dimethyl-2-cyclohexenone

(74) 3-(2-ethylhexanoyloxy)-2-phenyl-5,5-dimethyl-2-cyclohexenone

(75) 3-palmitoyloxy-2-phenyl-5,5-dimethyl-2-cyclohexenone

(76) 3-pivaloyloxy-2-(4'-methylphenyl)-5,5-dimethyl-2-cyclohexenone

Selected enol ester derivatives of 2-phenyl-1,3-cycloalkanedione compounds, representative of those useful in accordance with this invention were tested with respect to their miticidal, mite ovicidal and pre-emergent and post-emergent herbicidal activity. It was found that the compounds of the instant invention exhibited improved pesticidal activity, particularly miticidal activity, over structural similar prior art compounds.

Suspensions of the test compounds were prepared by dissolving one gram of compound in 50 milliliters of acetone in which had been dissolved 0.1 gram (10 percent of the weight of compound) of an alkylphenoxyethoxyethanol surfactant as an emulsifying or dispersing agent. The resulting solution was mixed into 160 millimiters of water to give roughly 200 milliliters of a suspension containing the compound in finely divided form. The thus prepared stock suspension contained 0.5 percent by weight of compound. The test concentrations employed in the tests described below were obtained by diluting the stock suspension with water. The test procedures were as follows:

Mite Foliage Spray Test

Adults and nymphal stages of the two-spotted mite (*Tetranychus urticae* (Koch), reared on Tendergreen bean plants at 80±5° F. and 50±5 percent relative humidity, were the test organisms. Infested leaves from a stock culture were placed on the primary leaves of two bean plants six to eight inches in height, growing in a two-and-a-half inch clay pot. 150–200 mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to provide suspensions containing the desired amount of test compound per million parts of final formulation. The potted plants (one pot per compound) were placed on a revolving turntable and sprayed with 100–110 milliliters of test compound formulation by use of a DeVilbis spray gun set at 40 psi. air pressure. This application, which lasted 30 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5° F. and 50±5 percent relative humidity for four days, after which, a mortality count of motile forms was made on the leaves of the test plants. Any individual which was capable of locomotion upon prodding was considered living.

Mite Ovicide Test

The test organism was the egg of the two-spotted mite (*Tetranychus urticae* (Koch)), as obtained from adults reared on Tendergreen bean plants under controlled conditions of 80±5° F. and 50±5 percent relative humidity. Heavily infested leaves from a stock culture were placed on the primary leaves of two bean plants six to eight inches in height growing in a two-and-a-half inch clay pot. Females were allowed to oviposit for a period of 48 hours and then the leaves of the infested plants were dipped late one afternoon and again the next morning in a solution containing 800 parts of tetraethyl pyrophosphate per million parts of water in order to destroy the reproductive forms and thus prevent further egg laying. This solution of tetraethyl pyrophosphate does not affect the viability of the eggs. The plants were allowed to dry thoroughly for several hours after the second dipping. The test compounds were formulated by diluting the stock suspension with water to give a suspension containing varying amounts of test compound per million parts of final formulation. The potted plants (one pot per compound) were placed on a revolving turntable and sprayed with 100–110 milliliters of test compound formulation by use of a DeVilbis spray gun set at 40 spig. air pressure. This application which lasted 30 seconds, was sufficient to wet the plants to run-off. As a control, 100–110 milliliters of a water solution containing acetone and emulsifier in the same concentrations as the test compound formulation, but containing no test compound, were also sprayed on plants infested with eggs. The sprayed plants were held at 80±5° F. and 50±5 percent relative humidity for four days, after which a microscopic examination was made of unhatched (dead) and hatched (living) eggs.

In these tests the pesticidal activity of the compounds against mites and mite eggs was rated as follows:
A = Excellent Control
B = Partial Control
C = No Control

PRELIMINARY HERBICIDE SEED GERMINATION TEST

The following seeds were used in this test:
Perennial rye grass—*Solium perenne*
Crabgrass—*Digitaria sanguinalis*
Red root pigweed—*Amaranthus retroflexus*
Mustard—*Brassica pincea* var. *foliosa* (Florida broadleaf)

Two seed-soil mixtures were prepared as follows:

Mixture I 196 cc. Rye grass seed
75 cc. Mustard seed
18,000 cc. Sifted, fairly dry soil

Mixture II 99 cc. Crabgrass seed
33 cc. Amaranthus
18,000 cc. Sifted, fairly dry soil Each of the above mixtures was rolled separately in 5 gallon containers for approximately one-half hour on ball mill to insure uniform mixing of seeds and soil. For each compound four 3-inch pots were filled with soil to within 1½ inches of top of pots. To two of these pots were added 70 cc. of Mixture I. To the remaining 2 pots were added 70 cc. of Mixture II. The seed-soil mixture was tamped firmly, and the pots were removed to the greenhouse and watered lightly. About 2 hours after planting, 25 milliliters of the test formulation were added to one pot containing Mixture I and one pot containing Mixture II. An equal volume of a water solution containing acetone and an emulsifier in the same concentration as the herbicidal mixture but without the candidate herbicide was also added to each of the soil-seed mixtures. These pots are used as check or control units. The test compounds were formulated by diluting the stock suspension with water to obtain the desired concentration of the compound in parts per million of the final formulation. Each compound was tested at the same concentration. Ten to twelve days after application of the chemical, injury was noted for each species by comparing treated versus untreated pots. Ratings were made according to the following designations:

5 = no seedling emerged
4 = few seedlings emerged and/or very severe stunting
3 = moderate reduction in stand and/or moderate stunting
2 = very slight reduction in stand and/or slight stunting
1 = no injury; seedlings appear no different with respect to stand or growth than untreated controls

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solutions to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table I below. The compound number listed in Table I corresponds to the number of the compound listed on pages 20 to 23, above.

TABLE I

Biocidal Activity and Physical Properties of Selected Enol Esters of 2-Phenyl-1,3-Cycloalkanedione Compounds

| Compound Number | M.P. (°C.) or Elemental Analysis | | Miticidal | | Post-emergent Herbicidal | | | | | Pre-emergent Herbicidal | | | |
|---|---|---|---|---|---|---|---|---|---|---|---|---|---|
| | | | Adult | Egg | Bean | Corn | Tomato | Cotton | Soybean | Rye | Crab-grass | Amaran-thus | Mustard |
| 49 | 58–59 | | B | B | 1 | 5 | 2 | 1 | 2 | 5 | 5 | 3 | 2 |
| 50 | 52.5–54.5 | | B | A | 2 | 4 | 1 | 2 | 2 | 5 | 5 | 4 | 3 |
| 51 | 69.0–71.0 | | A | A | — | 2 | — | 1 | 1 | 5 | — | — | 1 |
| 76 | 97.5–99 | | A | A | 1 | 1 | 1 | 1 | 1 | 5 | 5 | 1 | 1 |
| 52 | Cal'c for: | C      H | | | | | | | | | | | |
| | $C_{21}H_{28}O_3$ | 76.79  8.59 | A | A | 2 | 5 | 1 | 2 | 2 | 5 | 5 | 3 | 3 |
| | found: | 76.88  8.61 | | | | | | | | | | | |
| 53 | Cal'c for: | C      H | | | | | | | | | | | |
| | $C_{23}H_{32}O_3$ | 77.49  9.05 | A | A | 1 | 2 | 1 | 1 | 2 | 1 | 1 | 1 | 1 |
| | found: | 77.90  8.98 | | | | | | | | | | | |
| 54 | Cal'c for: | C      H | | | | | | | | | | | |
| | $C_{25}H_{36}O_3$ | 78.08  9.44 | A | A | 1 | 1 | 1 | 1 | 1 | 1 | 1 | 1 | 1 |
| | found: | 78.42  9.63 | | | | | | | | | | | |
| 55 | Cal'c for: | C      H | | | | | | | | | | | |

TABLE I-continued
Biocidal Activity and Physical Properties of Selected Enol Esters of 2-Phenyl-1,3-Cycloalkanedione Compounds

| Compound Number | M.P. (°C.) or Elemental Analysis | | | Miticidal | | Post-emergent Herbicidal | | | | | Pre-emergent Herbicidal | | | |
|---|---|---|---|---|---|---|---|---|---|---|---|---|---|---|
| | | | | Adult | Egg | Bean | Corn | Tomato | Cotton | Soybean | Rye | Crab-grass | Amaran-thus | Mustard |
| 56 | $C_{22}H_{32}O_3$ found: Cal'c for: | 77.49 77.56 C | 9.05 9.11 H | A | A | 2 | 3 | 1 | 2 | 2 | 5 | 5 | 3 | 3 |
| 57 | $C_{25}H_{36}O_3$ found: | 78.08 78.08 | 9.44 9.43 | A | A | 1 | 4 | 1 | 2 | 2 | 5 | 5 | 3 | 3 |
| 58 | 39–40 Cal'c for: | C | H | A | A | 1 | 2 | 1 | 1 | 1 | 5 | 5 | 3 | 3 |
| 59 | $C_{16}H_{17}ClO_3$ found: Cal'c for: | 65.65 64.07 C | 5.85 5.66 H | B | B | 2 | 2 | 1 | 1 | 3 | 3 | 4 | 2 | 2 |
| 60 | $C_{22}H_{29}ClO_3$ found: Cal'c for: | 70.10 70.42 C | 7.76 7.70 H | A | A | 1 | 1 | 1 | 1 | 1 | 1 | 1 | 1 | 1 |
| 61 | $C_{16}H_{17}ClO_3$ found: Cal'c for: | 65.64 65.58 C | 5.85 5.62 H | C | C | 3 | 1 | 1 | 1 | 3 | 1 | 1 | 1 | 1 |
| 62 | $C_{22}H_{29}ClO_3$ found: | 70.10 70.14 | 7.76 7.61 | A | A | 1 | 1 | 1 | 1 | 1 | 1 | 1 | 1 | 1 |
| 63 | 78–79 Cal'c for: | C | H | A | B | 1 | 1 | 1 | 1 | 1 | 1 | 1 | 1 | 1 |
| 64 | $C_{22}H_{28}ClO_3$ found: Cal'c for: | 64.23 64.46 C | 6.86 6.86 H | A | A | 1 | 2 | 1 | 1 | 1 | 1 | 1 | 1 | 1 |
| 66 | $C_{18}H_{22}O_3$ found: | 75.50 75.54 | 7.74 7.60 | B | A | 1 | 2 | 1 | 1 | 2 | 1 | 1 | 1 | 1 |
| 65 | 54–56.5 | | | B | B | 1 | 2 | 1 | 1 | 2 | 1 | 1 | 1 | 1 |
| 67 | 98.5–100 Cal'c for: | C | H | B | A | 1 | 1 | 1 | 1 | 1 | 1 | 1 | 1 | 1 |
| 68 | $C_{22}H_{30}O_3$ found: | 77.16 77.14 | 8.83 8.94 | A | A | 1 | 3 | 1 | 1 | 1 | 1 | 1 | 1 | 1 |
| 69 | 46–47.5 | | | A | A | 1 | 1 | 1 | 1 | 2 | 1 | 1 | 1 | 1 |
| 70 | 33.5–35.5 | | | A | A | 1 | 1 | 1 | 1 | 1 | 1 | 2 | 1 | 1 |
| 71 | 91.5–92.5 | | | B | B | 1 | 1 | 1 | 1 | 2 | 3 | 5 | 1 | 1 |
| 72 | 53–54.5 | | | B | B | 1 | 5 | 1 | 1 | 2 | 3 | 5 | 1 | 3 |
| 73 | 101.5–102 Cal'c for: | C | H | A | A | 1 | 1 | 1 | 1 | 1 | 1 | 1 | 1 | 1 |
| 74 | $C_{20}H_{26}O_3$ found: Cal'c for: | 76.40 76.17 C | 8.33 8.49 H | A | B | 1 | 3 | 1 | 1 | 2 | 4 | 5 | 1 | 2 |
| 75 | $C_{22}H_{30}O_3$ found: 32–34.0 | 77.16 77.16 | 8.83 8.83 | A | A | 1 | 2 | 1 | 1 | 2 | 1 | 1 | 1 | 1 |
| | | | | A | A | 1 | 1 | 1 | 1 | 1 | 1 | 1 | 1 | 1 |

It will be understood that the plant species employed in the above tests are merely representative of a wide variety of plant pest that can be controlled by the use of the compounds of this invention. The compounds contemplated in this invention may be applied as acaricides, pre-emergent and post-emergent herbicides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by acarids, particularly mites, upon plants or other material to which the pesticides are applied, and they have relatively high residual toxicity. With respect to plants, they are relatively safe to plants when used in sufficient amount to kill or repel the acarids or other plant pests, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants. The toxicants are so chemically inert that they are compatible with substantially any other constituents of the spray schedule. Mixtures of the active compounds may be employed if desired as well as combinations of the active compounds of this invention with other biologically active compounds.

What is claimed is:

1. A compound of the formula:

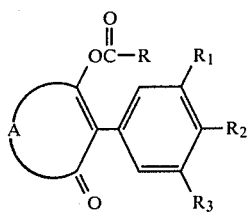

wherein:
R is an alkyl, alkenyl, alkynyl, cycloalkyl, cycloalkenyl, haloalkyl, phenyl or phenylalkyl group, all of which may be substituted with one or more alkyl, cyano, nitro, alkoxy, halogen, alkylthio, alkoxyalkyl, or alkylthioalkyl groups, provided that R may not include more than thirty aliphatic carbon atoms;

$R_1$, $R_2$, and $R_3$ may not individually include more than ten aliphatic carbon atoms and are individually hydrogen, haloalkyl, polyhaloalkyl, halogen or alkyl groups;

A is an alkylene or alkenylene chain containing two or three carbon atoms which chain may be substituted by one or more substituents which may be the same or different selected from:

(a) substituents which may not include more than ten aliphatic carbon atoms selected from: an alkyl, alkenyl, cycloalkyl or cycloalkenyl group, which groups may be further substituted by one or more cyano, halogen, nitro, alkoxy, aryloxy, alkylthio, arylthio, alkylsulfinyl, arylsulfinyl, alkylsulfonyl, arylsulfonyl, acylamido, or dialkylamino substituents in any combination; and a phenyl group which may be substituted by one or more alkyl, alkenyl, cycloalkyl, cycloalkenyl, cyano, halogen, nitro, alkoxy, aryloxy, alkylthio, arylthio, alkylsulfinyl, arylsulfinyl, alkylsulfonyl, arylsulfonyl, acylamido or dialkylamino substituents in any combination;

(b) a divalent alkylene or alkenylene group having from 2 to 20 carbon atoms completing a 3,4,5,6 or 7 membered carbon ring with the proviso that when A is a hydrocarbon chain containing two carbon atoms, a six membered fused polycyclic ring structure completed by a divalent butylene group may not have conjugated double bonds in said six membered ring, with the proviso that when A is a divalent alkylene group having 3 carbon atoms completing a 6 membered carbon ring substituted at the 5 position on said ring by two methyl groups; $R_1$ is chloro; $R_2$ and $R_3$ are hydrogen, then R cannot be a methyl group.

2. A compound according to claim 1 wherein R is an alkyl group having from 6 to 30 carbon atoms.

3. A compound according to claim 2 wherein A is substituted by one or more substituents selected from an alkyl, alkenyl, cycloalkyl or cycloalkenyl group which groups may be further substituted by one or more cyano, halogen, nitro, alkoxy, aryloxy, alkylthio, arylthio, alkylsulfinyl, arylsulfinyl, alkylsulfonyl, arylsulfonyl, acylamido, or dialkylamino substituents in any combination, and a phenyl group which may be substituted by one or more alkyl, alkenyl, cycloalkyl, cycloalkenyl, cyano, halogen, nitro, alkoxy, aryloxy, alkylthio, arylthio, alkylsulfinyl, arylsulfinyl, alkylsulfonyl, arylsulfonyl, acylamido or dialkylamino substituents.

4. A compound according to claim 2 wherein $R_1$ $R_2$ and $R_3$ are individually hydrogen, alkyl, halogen, or trihalomethyl groups.

5. A compound according to claim 4 of the following formula:

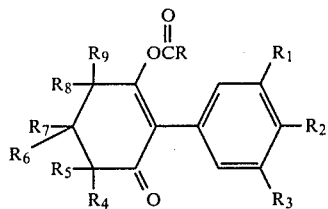

wherein:
$R_5$ and $R_8$ are hydrogen; and
$R_4$, $R_6$, $R_7$ and $R_9$ are individually hydrogen or $C_1$-$C_6$ alkyl groups.

6. A compound of the formula:

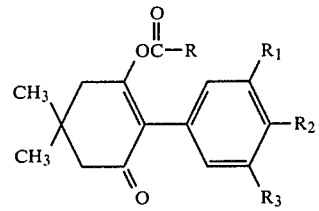

wherein:
R is an alkyl group having from 1 to 30 carbon atoms; and
$R_1$, $R_2$, and $R_3$ may not individually include more than ten aliphatic carbon atoms and are individually hydrogen, haloalkyl, polyhaloalkyl, halogen and alkyl groups, with the proviso that when $R_1$ is chloro and $R_2$ and $R_3$ are hydrogen, then R cannot be a methyl group.

7. A compound according to claim 6 wherein R is an alkyl group having from 6 to 30 carbon atoms.

8. A compound according to claim 7 wherein $R_1$, $R_2$, and $R_3$ are individually hydrogen, alkyl, halogen or trihalomethyl groups.

9. A compound according to claim 8 wherein $R_1$, $R_2$, and $R_3$ are individually hydrogen, methyl or halogen groups.

10. A compound according to claim 9 wherein R is a $C_6$-$C_{18}$ alkyl group.

11. A compound according to claim 10 wherein $R_1$, and $R_3$ are hydrogen; and
$R_2$ is a methyl, chloro, bromo or fluoro group.

12. 3-octanoyloxy-2-(4'-methylphenyl)-5,5-dimethyl-2-cyclohexenone.

* * * * *